(12) United States Patent
Green et al.

(10) Patent No.: US 7,309,773 B2
(45) Date of Patent: Dec. 18, 2007

(54) PROCESS FOR PREPARATION OF FLAX PROTEIN ISOLATE

(75) Inventors: Brent E. Green, Winnipeg (CA); Radka Milanova, Vancouver (CA); James Logie, Winnipeg (CA)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 189 days.

(21) Appl. No.: 10/902,102

(22) Filed: Jul. 30, 2004

(65) Prior Publication Data

US 2005/0058756 A1    Mar. 17, 2005

Related U.S. Application Data

(60) Provisional application No. 60/516,875, filed on Nov. 4, 2003, provisional application No. 60/491,564, filed on Aug. 1, 2003.

(51) Int. Cl.
*C07K 1/00* (2006.01)
(52) U.S. Cl. ..................................................... 530/377
(58) Field of Classification Search ................. 426/656
See application file for complete search history.

(56) References Cited

U.S. PATENT DOCUMENTS

| | | | |
|---|---|---|---|
| 2,573,072 A | 10/1951 | Vassel | 530/377 |
| 2,607,767 A | 8/1952 | Vassel | 530/377 |
| 4,085,229 A | 4/1978 | Staron | 426/46 |
| 4,285,862 A | 8/1981 | Murray et al. | |
| 4,370,267 A | 1/1983 | Lehnhardt et al. | |
| 5,925,401 A | 7/1999 | Kankaanpaa-Anttila et al. | |
| 6,005,076 A | 12/1999 | Murray | |
| 6,140,469 A | 10/2000 | Shen et al. | |
| 6,359,017 B1 | 3/2002 | Bruckner et al. | 424/757 |
| 2003/0109769 A1 | 6/2003 | Lowery et al. | |
| 2003/0149243 A1 | 8/2003 | Murray et al. | |
| 2004/0034200 A1 | 2/2004 | Logie et al. | |

FOREIGN PATENT DOCUMENTS

| | | |
|---|---|---|
| CA | 2451 190 | 11/2003 |
| CN | 1246504 | 3/2000 |
| JP | 55-124457 | 9/1980 |
| WO | WO 97/27761 | * 8/1997 |
| WO | WO 03/030652 | 4/2003 |
| WO | WO 03/088760 | 10/2003 |

OTHER PUBLICATIONS

JP AGR. & Food Chem, (Thanh, et al), vol. 24, No. 6, 1976, pp. 1117-1121.

* cited by examiner

*Primary Examiner*—Karen Cochrane Carlson
*Assistant Examiner*—Agnes B. Rooke
(74) *Attorney, Agent, or Firm*—Sim & McBurney; Michael I. Stewart

(57) ABSTRACT

Flax protein isolates are obtained in a procedure in which flax oil seeds are initially extracted to remove mucilage therefrom prior to crushing to recover the oil and produce a meal. The flax protein meal then is processed to recover a flax protein isolate therefrom.

17 Claims, 5 Drawing Sheets

PROCESS FOR PREPARATION OF FLAX PROTEIN ISOLATE

REFERENCE TO RELATED APPLICATIONS

This application claims priority pursuant to 35 USC 119(e) from U.S. Patent Applications No. 60/491,564 filed Aug. 1, 2003 and 60/516,875 filed Nov. 4, 2003.

FIELD OF INVENTION

The present invention relates to the recovery of flax protein isolates from flax oil seed meal.

BACKGROUND OF THE INVENTION

In U.S. patent application Ser. No. 10/266,677 filed Oct. 9, 2002 (WO 03/030652), assigned to the assignee hereof and the disclosure of which is incorporated herein by reference, there is described the preparation of a flax protein isolate. As set forth therein, there is provided a flax oil seed protein isolate having a protein content of at least about 90 wt %, preferably at least about 100 wt %, as determined by Kjeldahl nitrogen×6.25 (N×6.25) on a dry weight basis.

In such process, yields of flax protein isolate were limited because of the inability to concentrate the protein solution to high protein contents owing to the presence of water-soluble mucilage. Flax seed mucilage is a gummy substance consisting substantially of polysaccharides. The presence of the mucilage in protein products separated from flax oil seed meal by other processes makes it difficult to produce products with protein contents high enough to be classified as isolates.

Flax seed is known to contain about 34 to about 37 wt % proteins and several different protein components, distinguished by different sedimentation coefficients (S), have been identified. These proteins include a 12S globulin, known as linin, and 2S albumin, known as colinin.

Linola® oil seed, distributed by Agricore United, is a mutant of flax oil seed in which the fatty acid composition has been changed and linolenic acid (C18:3) has been substantially reduced from about 50% in conventional flax oil seed to about 2%, through traditional breeding procedures. These modifications were made to provide, from the resulting Linola oil seed, an edible polyunsaturated oil substantially similar to sunflower oil in fatty acid composition.

SUMMARY OF THE INVENTION

It has now surprisingly been found that, if an initial extraction of the flax seed at elevated temperature using a mildly-alkaline solution of sodium bicarbonate to remove mucilage is effected, then a much higher concentration of concentrated aqueous protein solution can be produced, enabling improved yields of flax protein isolate to be obtained. In addition, a flax protein isolate can be produced from flax protein meal by isoelectric precipitation or by a micellar route.

It has now also been found that the predominant protein component of flax protein isolates of the invention is a 7S protein, which appears to be half of the 12S globulin known as linin, and which has a molecular weight of approximately 162,000 to 169,000 Da, as determined by HPLC Retention Times compared to BioRad animal protein standards. Other protein components of flax protein isolates of the invention include linin, having a molecular weight of approximately 415,000 to 440,000 Da, as determined by HPLC Retention Times compared to BioRad animal protein standards and colinin, having a molecular weight of approximately 16,000 to 17,000 Da, as determined by HPLC Retention Times compared to BioRad animal protein standard.

It has now further been found that the relative proportions of the protein components are similar between protein micellar mass (PMM)-derived flax protein isolate and supernatant-derived flax protein isolate of the invention.

In particular, it has been found that PMM-derived flax protein isolate having a protein content of at least about 90 wt % (N×6.25), preferably at least about 100 wt %, has a protein component content of about 65 to 95 wt % of 7S flax protein (half of linin), about 0 to 20 wt % of linin and about 0 to 20 wt % of colinin. It has been found that supernatant-derived flax protein isolate having a protein content of at least about 90 wt % (N×6.25), preferably at least about 100 wt %, has a protein component content of about 65 to 95 wt % of 7S flax protein (half of linin), about 0 to 20 wt % of linin and about 0 to 20 wt % of colinin.

The similarity in the protein component profiles for the PMM-derived and the supernatant-derived flax protein isolates results in similar behaviour in environments where the flax protein isolates are employed. The similar protein content profiles enable the combining of PMM-derived and supernatant-derived flax protein isolates in any desired proportion without altering the composition, thus resulting in an increased yield for the process.

PMM-derived, supernatant-derived and iso-electric precipitation (IEP)-derived flax protein isolates have a very similar amino acid profile. The amino acid profiles obtained are set forth below in the Examples.

The present invention provides a flax protein isolate having a unique protein profile and a procedure for preparation of the same involving an initial extraction of the oil seed. A protein isolate is defined as a protein containing at least about 90 wt % protein at a Kjeldahl nitrogen conversion rate of N×6.25. The term "protein content" as used herein refers to the quantity of protein in the protein isolate expressed on a dry weight basis.

The flax protein isolate produced according to the process herein may be used in conventional applications of protein isolates, such as, protein fortification of processed foods, emulsification of oils, body formers in baked goods and foaming agents in products which entrap gases. In addition, the protein isolate may be formed into protein fibers, useful in meat analogs, may be used as an egg white substitute or extender in food products where egg white is used as a binder. The flax protein isolate may be used as nutritional supplements. Other uses of the flax protein isolate are in pet foods, animal feed and in industrial and cosmetic applications and in personal care products.

GENERAL DESCRIPTION OF INVENTION

Figure 1:
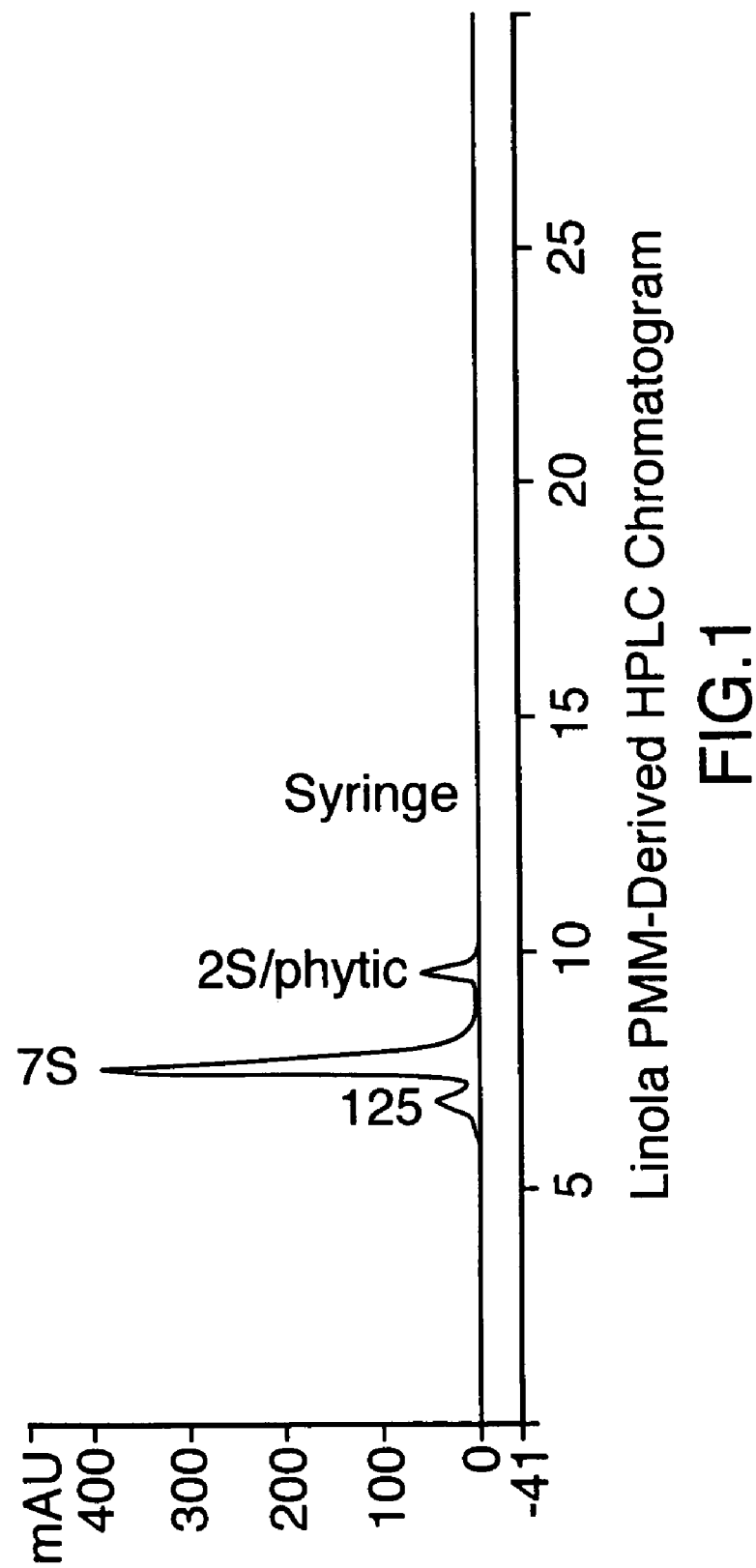
FIGS. 1 and 2 are HPLC chromatograms of Linola isolates, with FIG. 1 being that for a PMM-derived Linola protein isolate and FIG. 2 being that for a supernatant-derived Linola protein isolate.

The initial extraction of the flax seed is effected using an aqueous solution, generally having a pH of about 7.5 to about 9, preferably at the natural pH of the aqueous solution of the alkaline material, at an elevated temperature of about 30° to about 70° C., preferably at about 50° C. The extraction of flax oil seed may be effected at seed to solution ratio of about 1:1 to about 1:20, preferably about 1:5 to about 1:10, using an aqueous solution containing about 0.2 to about 0.7 M mildly-alkaline material. Preferably, an aqueous solution of sodium bicarbonate having a concentration of about 0.5 M is used at about 50° C. in a ratio of flax seed to solution of about 1:8.

After a first extraction of the oil seed, generally by mixing with stirring of the oil seed in the aqueous alkaline solution, for about 15 to about 60 minutes, preferably about 30 to about 60 minutes, the extraction is preferably repeated with fresh aqueous alkaline solution until no further mucilage is extracted from the oil seeds.

The extracted oil seeds then are processed to recover the oil and to provide an oil seed meal from which a flax protein isolate may be produced.

One procedure whereby the flax protein isolate may be formed from the flax oil seed meal is by isoelectric precipitation. Prior to effecting the initial removal of mucilage as provided herein, the applicants had not been able to produce a flax protein isolate by isoelectric precipitation processing of flax oil seed meal. Isoelectric precipitation is commonly used to prepare other protein isolates, for example, soy protein isolate.

In such isoelectric precipitation, the flax oil seed meal, or linola oil seed meal, is extracted with an aqueous alkaline solution, generally an aqueous sodium hydroxide solution having a pH of about 8 to about 12, preferably about 9 to about 11, at a temperature of about 0° to about 40° C., preferably about 15° to about 25° C., at a meal concentration of about 2.5 to about 10% w/v, preferably about 5% w/v.

Following extraction of the meal, residual meal is separated from the aqueous protein solution in any convenient manner, such as by employing vacuum filtration, followed by centrifugation and/or filtration to remove residual meal. The separated residual meal may be dried for disposal.

The flax protein solution is then acidified to a pH of about 3 to about 5, preferably about 4, using any convenient acid, such as hydrochloric acid, to cause the formation of a precipitate of flax or linola protein isolate. The precipitate is removed from supernatant and dried. The dried isoelectric precipitation (IEP)-derived flax protein isolate has a high protein content, in excess of about 90 wt % (N×6.25), preferably at least about 100 wt %.

Alternatively and preferably, the flax protein isolate is prepared following the procedure described in the aforementioned copending U.S. patent application Ser. No. 10/266,677. The process may be effected in a series of batch operations or as a continuous or semi-continuous process.

The initial step of the process of producing the flax protein isolate according to the procedure of the aforementioned application, involves solubilizing proteinaceous material from flax oil seed meal. The proteinaceous material recovered from flax seed meal may be the protein naturally occurring in flax seed or the proteinaceous material may be a protein modified by genetic manipulation but possessing characteristic hydrophobic and polar properties of the natural protein. The flax meal may be any flax meal resulting from the removal of flax oil from flax oil seed with varying levels of non-denatured protein, resulting, for example, from hot hexane extraction or cold oil extrusion methods. The removal of flax oil from flax oil seed usually is effected as a separate operation from the protein isolate recovery procedure described herein.

Protein solubilization is effected most efficiently by using a salt solution since the presence of the salt enhances the removal of soluble protein from the oil seed meal. The salt usually is sodium chloride, although other salts, such as, potassium chloride, may be used. The salt solution has an ionic strength of at least about 0.10 M, preferably at least about 0.15 M, generally up to about 2.0 M to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the salt solution which causes maximum protein solubilization varies depending on the salt concerned and the oil seed meal chosen.

In view of the greater degree of dilution required for protein precipitation with increasing ionic strengths, it is usually preferred to utilize an ionic strength value less than about 1.0 and more preferably a value of about 0.15 to about 0.6.

In a batch process, the salt solubilization of the protein is effected at a temperature of above about 0° C. and preferably up to about 35° C., preferably accompanied by agitation to decrease the solubilization time, which is usually about 10 to about 90 minutes. It is preferred to effect the solubilization to extract substantially the maximum amount of protein from the oil seed meal, so as to improve product yield. The upper preferred temperature limit of about 35° C. is chosen since the process becomes uneconomic at higher temperature levels in a batch mode.

In a continuous process, the extraction of the protein from the flax oil seed meal is carried out in any manner consistent with effecting a continuous extraction of protein from the flax oil seed meal. In one embodiment, the flax oil seed meal is continuously mixed with a salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially the maximum amount of protein from the flax oil seed meal. The solubilization in the continuous procedure preferably is effected at elevated temperatures, generally up to about 60° C. or more.

The aqueous salt solution and the flax oil seed meal have a natural pH of about 5 to about 7 to enable a protein isolate to be formed by the micellar route, as described in more detail below. The optimal pH value for maximum yield of flax or linola protein isolate varies depending on the flax oil seed meal chosen.

At and close to the limits of the pH range, protein isolate formation occurs only partly through the micelle route and in lower yields than attainable elsewhere in the pH range. For these reasons, pH values of about 5.3 to about 6.2 are preferred.

The pH of the salt solution may be adjusted to any desired value within the range of about 4 to about 7 for use in the extraction step by the use of any convenient acid, usually hydrochloric acid, or alkali, usually sodium hydroxide, as required.

The concentration of oil seed meal in the salt solution during the solubilization step may vary widely. Typical concentration values are about 5 to about 15% w/v.

The protein extraction step with the aqueous salt solution has the additional effect of solubilizing fats which may be present in the flax seed meal, which then results in the fats being present in the aqueous phase.

The protein solution resulting from the extraction step generally has a protein concentration of about 5 to about 40 g/L, preferably about 10 to about 30 g/L.

The aqueous phase resulting from the extraction step then may be separated from the residual flax oil seed meal, in any convenient manner, such as by employing vacuum filtration, followed by centrifugation and/or filtration to remove residual meal. The separated residual meal may be dried for disposal.

Where the flax seed meal contains significant quantities of fat, then the defatting steps described in U.S. Pat. Nos. 5,844,086 and 6,005,076, assigned to the assignee hereof and the disclosures of which are incorporated herein by reference, for canola, may be effected on the separated aqueous protein solution and on the concentrated aqueous protein solution discussed below.

As an alternative to extracting the flax oil seed meal with an aqueous salt solution, such extraction may be made using water alone, although the utilization of water alone tends to extract less protein from the flax oil seed meal than the aqueous salt solution. Where such alternative is employed, then the salt, in the concentrations discussed above, may be added to the protein solution after separation from the residual flax oil seed meal in order to maintain the protein in solution during the concentration step described below.

The aqueous protein solution then is concentrated to increase the protein concentration thereof while maintaining the ionic strength thereof substantially constant. Such concentration generally is effected to provide a concentrated protein solution having a protein concentration of at least about 150 g/L, preferably at least about 250 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3,000 to about 100,000 daltons, preferably about 5,000 to about 10,000 daltons, having regard to differing membrane materials and configurations, and, for continuous operation, dimensioned to permit the desired degree of concentration as the aqueous protein solution passes through the membranes.

The concentrated protein solution then may be subjected to a diafiltration step using an aqueous salt solution, usually a sodium chloride solution, of the same molarity and pH as the extraction solution. Such diafiltration may be effected using from about 2 to about 20 volumes of diafiltration solution, preferably about 5 to about 10 volumes of diafiltration solution. In the diafiltration operation, further quantities of contamination are removed from the aqueous protein solution by passage through the membrane with the permeate. The diafiltration operation may be effected until no significant further quantities of contaminants are present in the permeate. Such diafiltration may be effected using a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diaflitration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %.

The concentration step and the optional dialfiltration step may be effected at any convenient temperature, generally about 15° to about 60° C., and for the period of time to effect the desired degree of concentration. The temperature and other conditions used, to some degree, depend upon the membrane equipment used to effect the concentration and the desired protein concentration of the solution.

As is well known, ultrafiltration and similar selective membrane techniques permit low molecular weight species to pass therethrough while preventing higher molecular weight species from so doing. The low molecular weight species include not only the ionic species of the food grade salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through, having regard to the different membrane materials and configurations.

The concentrated and optionally diafiltered protein solution may be subjected to pasteurization to kill any bacteria which may have been present in the original meal as a result of storage or otherwise and extracted from the meal into the flax protein isolate solution in the extraction step. Such pasteurization may be effected under any desired pasteurization conditions. Generally, the concentrated and optionally diafiltered protein solution is heated to a temperature of about 55° to about 70° C., preferably about 60° to about 65° C., for about 10 to about 15 minutes, preferably about 10 minutes. The pasteurized concentrated protein solution then may be cooled for further processing as described below, preferably to a temperature of about 25° to about 40° C.

Depending on the temperature employed in the concentration step, the concentrated protein solution may be warmed to a temperature of at least about 20°, and up to about 60° C., preferably about 25° to about 40° C., to decrease the viscosity of the concentrated protein solution to facilitate performance of the subsequent dilution step and micelle formation. The concentrated protein solution should not be heated beyond a temperature above which the temperature of the concentrated protein solution does not permit micelle formation on dilution by chilled water. The concentrated protein solution may be subject to a further defatting operation, if required, as described in U.S. Pat. Nos. 5,844,086 and 6,005,076.

The concentrated protein solution resulting from the concentration step and optional defatting step then is diluted to effect micelle formation by mixing the concentrated protein solution with chilled water having the volume required to achieve the degree of dilution desired. The concentrated protein solution is diluted by about 15 fold or less, preferably about 10 fold or less.

The chilled water with which the concentrated protein solution is mixed has a temperature of less than about 15° C., generally about 3° to about 15° C., preferably less than about 10° C., since improved yields of protein isolate in the form of protein micellar mass are attained with these colder temperatures at the dilution factors used.

In a batch operation, the batch of concentrated protein solution is added to a static body of chilled water having the desired volume, as discussed above. The dilution of the concentrated protein solution and consequential decrease in ionic strength causes the formation of a cloud-like mass of highly associated protein molecules in the form of discrete protein droplets in micellar form. In the batch procedure, the protein micelles are allowed to settle in the body of chilled water to form an aggregated, coalesced, dense, amorphous, sticky gluten-like protein micellar mass (PMM). The settling may be assisted, such as by centrifugation. Such induced settling decreases the liquid content of the protein micellar mass, thereby decreasing the moisture content generally from about 70% by weight to about 95% by weight to a value of generally about 50% by weight to about 80% by weight of the total micellar mass. Decreasing the moisture content of the micellar mass in this way also decreases the occluded salt content of the micellar mass, and hence the salt content of dried isolate.

Alternatively, the dilution operation may be carried out continuously by continuously passing the concentrated protein solution to one inlet of a T-shaped pipe, while the diluting water is fed to the other inlet of the T-shaped pipe, permitting mixing in the pipe. The diluting water is fed into the T-shaped pipe at a rate sufficient to achieve the desired degree of dilution of the concentrated protein solution.

The mixing of the concentrated protein solution and the diluting water in the pipe initiates the formation of protein micelles and the mixture is continuously fed from the outlet from the T-shaped pipe into a settling vessel, from which, when full, supernatant is permitted to overflow. The mixture preferably is fed into the body of liquid in the settling vessel in a manner which minimizes turbulence within the body of liquid.

In the continuous procedure, the protein micelles are allowed to settle in the settling vessel to form an aggregated, coalesced, dense, amorphous, sticky, gluten-like protein micellar mass (PMM) and the procedure is continued until a desired quantity of the PMM has accumulated in the bottom of the settling vessel, whereupon the accumulated PMM is removed from the settling vessel.

The settled isolate is separated from the residual aqueous phase or supernatant, such as by decantation of the residual aqueous phase from the settled mass or by centrifugation. The PMM may be used in the wet form or may be dried, by any convenient technique, such as spray drying, freeze drying or vacuum drum drying, to a dry form. The dry flax protein isolate has a high protein content, in excess of about 90 wt % protein, preferably at least about 100 wt % protein (N×6.25), and is substantially undenatured (as determined by differential scanning calorimetry). The dry flax protein isolate isolated from fatty oil seed meal also has a low residual fat content, when the procedures of U.S. Pat. Nos. 5,844,086 and 6,005,076 are employed, which may be below about 1 wt %.

The supernatant from the PMM formation and settling step contains significant amounts of flax protein, not precipitated in the dilution step, and the supernatant may be processed to recover additional quantities of protein therefrom.

In such procedure, the supernatant from the dilution step, following removal of the PMM, may be concentrated to increase the protein concentration thereof. Such concentration is effected using any convenient selective membrane technique, such as ultrafiltration, using membranes with a suitable molecular weight cut-off permitting low molecular weight species, including the food grade salt and other non-proteinaceous low molecular weight materials extracted from the source material, to pass through the membrane, while retaining flax protein in the solution. Ultrafiltration membranes having a molecular weight cut-off of about 3,000 to 100,000 daltons having regard to differing membranes and configurations, may be used. Concentration of the supernatant in this way also reduces the volume of liquid required to be dried to recover the protein, and hence the energy required for drying. The supernatant generally is concentrated to a protein content of about 50 to 300 g/L, preferably about 100 to about 200 g/L, prior to drying.

The concentrated supernatant may be dried by any convenient technique, such as spray drying, freeze drying or vacuum drum drying, to a dry form to provide a further flax protein isolate. Such further flax protein isolate has a high protein content, usually in excess of about 90 wt % protein (N×6.25), preferably at least 100 wt %, and is substantially undenatured (as determined by differential scanning calorimetry). If desired, the wet PMM may be combined with the concentrated supernatant prior to drying the combined protein streams by any convenient technique to provide a combined flax protein isolate. The combined flax protein isolate has a high protein content, in excess of about 90 wt % (N×6.25), preferably at least about 100 wt %, and is substantially undenatured (as determined by differential scanning calorimetry).

In another alternative procedure, a portion only of the concentrated supernatant may be mixed with at least part of the PMM and the resulting mixture dried. The remainder of the concentrated supernatant may be dried as any of the remainder of the PMM. Further, dried PMM and dried supernatant also may be dry mixed in any desired relative proportions.

By operating in this manner, a number of flax protein isolates may be recovered, in the form of dried PMM, dried supernatant and dried mixtures of various proportions by weight of PMM and supernatant, generally from about 5:95 to about 95:5 by weight, which may be desirable for attaining differing functional and nutritional properties.

Alternatively, the procedure described in copending U.S. Patent Application No. 60/544,346 filed Feb. 17, 2004, assigned to the assignee hereof and the disclosure of which is incorporated herein by reference, for the recovery of canola protein isolate, may be used to recover the flax protein isolate. According to the procedure described therein, the concentrated protein solution resulting from the protein solution concentration step is dried directly, rather than processing to produce PMM and separately processing the supernatant. Drying of the concentrated protein solution, which may also be optionally diafiltered and defatted, as described above, may be effected in any convenient manner, such as spray drying, freeze drying or vacuum drum drying.

Since the protein isolates which are formed by the direct drying procedure are generally of lesser purity, in particular, a higher salt content, than obtained by the procedure described above, they are preferably used in non-human applications, although the protein isolates may be processed to reduce their salt content by any convenient procedure, such as by dialysis.

The relative quantities of the respective proteins in any given protein isolate may be determined by any convenient analytical technique, such as an analytical separation technique. The most common of these techniques uses selective media in a column that permits separation based on size. For gel permeation chromatography (GPC) applications, spherical gel-like materials are used. Where pressure is used, as in high pressure liquid chromatography (HPLC), then a rigid media is used. The latter technique also is known as size exclusion chromatography (SEC). The results obtained using such techniques on samples of flax protein isolate prepared as described herein are contained in the Examples below.

The PMM-derived flax protein isolate and the supernatant-derived flax protein isolate predominantly consist of the 7S flax protein (half of linin), having a molecular weight of approximately 162,000 to 169,000 Da, with minor quantities of linin, having a molecular weight of approximately 415,000 to 440,000 Da, and colinin, having a molecular weight of approximately 16,000 to 17,000 Da. In general, the PMM-derived protein contains:

about 65 to 95 wt % of 7S flax protein (half of linin);
about 0 to 20 wt % of linin; and
about 0 to 20 wt % of colinin.

In general, the supernatant-derived protein contains:

about 65 to 95 wt % of 7S flax protein (half of linin);
about 0 to 20 wt % of linin; and
about 0 to 20 wt % of colinin.

EXAMPLES

Example 1

This Example illustrates the removal of mucilage from Linola oil seed meal.

Linola oil seed was washed using varying concentration levels of sodium bicarbonate by mixing aqueous sodium bicarbonate with a seed: solvent ratio of 1:8 with Linola oil seed for one hour at 50° C. using an overhead mixer set at high speed.

Washes were done at each concentration of aqueous sodium bicarbonate solution tested in order to compare the amount of mucilage recovered from the seeds. A total of 500 g of linola was washed in 4 L of sodium bicarbonate at each concentration.

The supernatant from each wash was decanted and 100 ml from each supernatant was diluted 1:1 with 88% ethanol to precipitate any solubilized mucilage. The mucilage then was collected and dried to calculate the total amount of mucilage removed from the seeds.

The amounts extracted at the various concentration of sodium bicarbonate solution is shown in Table I:

TABLE I

Weight of mucilage removed during first wash at each concentration

| Sodium bicarbonate concentration | Weight of mucilage (g) |
| --- | --- |
| 0.1 M | 16.0 g |
| 0.3 M | 16.4 g |
| 0.5 M | 32.0 g |

As may be seen from Table I, a sodium bicarbonate concentration of 0.5 M is much more effective for removing mucilage than lower concentrations. In addition, at the 0.5 M concentration, the seed still had the slimy feel to it that is attributed to mucilage. A second, identical wash was done and another 34 grams of mucilage was removed. Following this second wash, a third wash was done and another 36.4 grams of mucilage was removed. A fourth wash yielded very little mucilage, indicating complete removal of mucilage from the 500 grams of linola seed. A total of 102.8 grams of mucilage was removed.

Following these washes, the seed did not have the "slimy" feel that mucilage imparts, providing another good indication that most of the mucilage had been removed.

Example 2

This Example illustrates the preparation of a flax meal in accordance with one embodiment of the invention.

25 kg of Linola oil seed, variety 2047, was added to 200 L of 0.5 M sodium bicarbonate at 50° C. in a 400 L mixing tank. The slurry was stirred vigorously for one hour. After settling, the aqueous phase was decanted and the waste was discarded. A one-liter portion of the decanted aqueous phase was diluted with an equal volume of ethanol, to precipitate mucilage to provide a rough estimate of the amount of mucilage recovered.

After decanting the aqueous phase, the seed was rinsed twice with hot tap water to remove any residual wash solution. The procedure of sodium bicarbonate extraction, separation and washing was repeated five times. The seed was then washed four times with hot tap water to remove any residual wash and mucilage. The seed was found to have lost its characteristic slimy feel, providing a good indication that the mucilage had been removed.

It was found that each successive aqueous sodium bicarbonate wash removed less mucilage than the previous one and that, by the fifth wash, very little mucilage was precipitated from the one-liter portion of wash solution when diluted with ethanol, providing a good indication that most of the mucilage had been removed from the seed.

The seed then was dried, washed and defatted to remove the oil from the seed.

Example 3

This Example illustrates the preparation of a Linola protein isolate from mucilage-reduced meal by iso-electric precipitation.

10 kg of the defatted Linola oil seed meal, prepared as described in Example 2, was added to 200 L of 0.15 M NaCl solution at room temperature and the pH of the mixture was adjusted to 11.0 with 50 wt % sodium hydroxide solution. The slurry was stirred for one hour, after which the extracted meal was permitted to settle from the resulting protein solution for one hour.

100 L of protein solution, having a protein content of 13 g/L, was then decanted and filtered through 20 and 0.2 μm filters in a filter press in order to clarify the solution. The clarified solution then was placed in a cooler at 4° C. for 16 hours to permit any oil present to rise to the surface, where it could be skimmed off. Very little oil was seen, indicating a very effective defatting step.

The pH of the protein solution at ambient temperature was then adjusted to 4.0 using 3 N HCl and the protein immediately began to precipitate by a change of colour of the solution from a golden yellow colour to milky white. Once the mixing was stopped, the protein precipitated rapidly from the solution. After a two-hour settling period, the supernatant was decanted and analyzed for protein content.

Following removal of supernatant, 10 L of pellet material was centrifuged at 10,000×g for 5 minutes to decrease the residual supernatant content of the precipitated protein. The resulting pellet was reconstituted in 4 L of water and spray dried to provide 293 g of dried IEP-derived Linola protein isolate. The protein content of the spray dried protein was 101 wt % (N×6.25) d.b.

Example 4

This Example illustrates the functional properties of the Linola protein isolate produced in Example 3.

The EP-derived Linola protein isolate produced according to the procedure of Example 3 (IEP Linola) was tested for functional properties of foaming and oil holding capacity in comparison to typical samples of PMM-derived and supernatant-derived canola protein isolates (CPI) produced according to the process described in pending U.S. patent application Ser. No. 10/137,391 filed May 3, 2002 (WO 02/089597), assigned to the assignee hereof and the disclosure of which is incorporated herein by reference.

The test procedures employed are those set forth in copending U.S. patent application Ser. No. 10/137,306 filed May 3, 2002 (WO 02/089597), assigned to the assignee hereof and the disclosure of which is incorporated herein by reference.

For foaming, the procedure utilized is that described in Phillips et al, J. Food Sci. 55:1441, 1990. 3.75 g samples of protein isolates were placed into individual 150 ml beakers. 60 ml of 0.075 M NaCl solution was added to the protein, by initially making a paste to dissolve the protein with a few ml of liquid. The mixture was mixed on a stirrer with a magnetic stir bar for 10 minutes. The pH of the solution was adjusted to 7.00 with 0.1 M NaOH, and the solution stirred for another 10 minutes. The pH was re-adjusted to 7.00 and the volume of liquid was brought up to 75 ml with the required amount of 0.075M NaCl to yield a 5% w/v protein solution. The 75 ml of solution was poured into a Hobart Mixer bowl and the combined weight of solution, bowl and whisk attachment was recorded. The protein solution was whipped on speed 3 for 5 minutes.

Sufficient foam was gently scooped out to fill two tared 125 ml measuring cups using a rubber spatula. Excess foam was scraped off using the flat end of a large knife to level the top of the foam even with the top of the measuring cup and the weight of the foam was recorded. The foam was gently returned to the mixing bowl and whipped for another 5 minutes. This procedure then was repeated. The foam was gently returned to the mixing bowl and whipped for a further 5 minutes for 15 minutes in all. The procedure again was repeated.

The overrun was calculated from the following equation:

$$\% \text{ Overrun} = \frac{(\text{wt } 125 \text{ mL protein}) - (\text{wt } 125 \text{ ml foam})}{(\text{wt } 125 \text{ ml foam})} \times 100$$

The stability of the foam was also tested. The protein solution was prepared in the same manner as described for the % overrun measurements except the protein solution was whipped for 15 minutes on level 3. Using a rubber spatula, the foam was carefully transferred to into a 1 L long-necked funnel placed on top of a 250 ml graduated cylinder. A small amount of quartz wool was placed in the top of the funnel spout to prevent foam from draining while still allowing drainage of the liquid.

The volume of liquid that was collected in the graduated cylinder at 5, 10 and 15 minutes was measured. The volume held in the wool was added to the final volume.

For oil holding capacity, the procedure used in this Example is that described in Swift et al, Food Technol. 15,436-72 (1961).

The recipe set forth in Table II was used to prepare an emulsion:

TABLE II

| Ingredient | Weight Added (g) |
| --- | --- |
| Protein Isolate | 0.5 |
| Vinegar (No Name 5% acetic acid) | 55.2 |
| Canola Oil (CSP Foods) | N/D |
| Sugar (Rogers fine granulated | 4.1 |
| Salt (Sifto) | 1.2 |
| Distilled Water | 52.4 |

N/D = not determined

The sugar, salt and protein isolate were dry blended in a 600 ml beaker. The water and vinegar were mixed, by initially making a paste to dissolve the protein with a few ml of liquid. The mixture was mixed on a stirrer using a magnetic bar for 5 minutes. A 2000 ml beaker was filled with canola oil and the weight recorded. A suction hose was placed in the oil.

The dispensing end of the hose was attached to a homogenizer and the pump was primed with oil using setting #1 to dispense approximately 40 to 50 ml/min. At the same time, the homogenizer (Silverson LHRT) was turned to 5,000 rpm and the pump switched on to disperse the oil. The point at which the emulsion was most viscous was visually observed. At the point of inversion, the pump and homogenizer were immediately switched off. The end of the suction hose was pinched with a clip to keep the oil in it and the weight of oil left in the 200 ml beaker was determined.

The results obtained are set forth in Tables III and IV below:

TABLE III

IEP-derived Linola Protein Isolate vs. Canola PMM-derived CPI

| Batch | % Overrun (Foam Volume) | Foam Stability (Ml drainage at 15 minutes) | Oil Holding Capacity (Ml oil/100 mg protein) | Globular size (μM) |
| --- | --- | --- | --- | --- |
| CPI-1 | 1471.8 | 17.5 | 147.7 | 18.9 |
| CPI-2 | 1030.4 | 32.7 | 190.5 | 29.1 |
| CPI-3 | 1216.5 | 24.0 | 119.8 | 24.3 |
| CPI-4 | 1051.2 | 45.3 | 115.4 | 21.6 |
| CPI-5 | 1091.6 | 35.3 | 124.5 | 28.0 |
| CPI-6 | 1196.1 | 34.0 | 166.9 | 24.6 |
| IEP-derived Linola | 1770.9 | 0.67 | 118.9 | 59.0 |

TABLE IV

IEP-derived Linola Protein Isolate vs. Canola Supernatant-derived CPI

| Batch | % Overrun (Foam Volume) | Foam Stability (Ml drainage at 15 minutes) | Oil Holding Capacity (Ml oil/100 mg protein) | Globular size (μM) |
| --- | --- | --- | --- | --- |
| CPI-7 | 2603.6 | 22.7 | 67.2 | 72.6 |
| CPI-8 | 1984.8 | 21.3 | 53.6 | 151.7 |
| CPI-9 | 1924.4 | 22.0 | 43.3 | 151.7 |
| CPI-10 | 1889.2 | 17.3 | 41.3 | 192.4 |
| IEP-derived Linola | 1170.9 | 0.67 | 118.9 | 59.0 |

As may be seen from Table III, the IEP Linola protein isolate had superior foam properties to the PMM-derived canola protein isolates, with foam higher volume and less drainage (better stability). The oil holding capacity of the IEP Linola protein isolate was comparable to the PMM-derived canola protein isolate but it had a larger globular size.

As may be seen from Table IV, the foam volume produced by the IEP Linola protein isolate was less than that produced by the supernatant-derived canola protein isolate, but the foam was much more stable. The Linola protein isolate had superior emulsification properties to the supernatant-derived canola protein isolate. The oil holding capacity of the Linola protein isolate was approximately twice as high as the supernatant-derived canola protein isolate and had a smaller globular size.

Example 5

This Example illustrates the preparation of a Linola protein isolate from mucilage-reduced meal by a micellar route.

4 kg of the defatted Linola oil seed meal, prepared as described in Example 2, was added to 80 L of 0.5 M NaCl solution at room temperature (5% w/v). The slurry was mixed for one hour, following which the slurry was allowed to settle for ½ hour and the aqueous protein solution decanted. The decanted aqueous protein solution had a protein content of 7.1 g/L and a volume of 55 L. The solution was filtered through 20 µM filter pads in a filter press to remove suspended solids. The press was flushed with 20 L of water to provide 75 L of a filtrate having a protein content of 5.28 g/L.

The filtrate was subjected to ultrafiltration using 300 daltons molecular weight cut-off ultrafiltration membranes to concentrate the solution to 1.3 L of concentrated aqueous protein solution (retentate) having a protein content of 174 g/L. The retentate then was diluted into 9 volumes of 4° C. water, which produced a white cloud of protein micelles.

A settling period of 16 hours was permitted after which the supernatant was decanted and centrifuged to recover as much of the precipitated material as possible to provide 11 L of supernatant having a protein content of 1.11 g/L. The Linola protein isolate pellet obtained from the precipitation step also was centrifuged to reduce its volume to a minimum level.

The Linola protein isolate pellet was dried to produce 81 g of dried protein, representing a 20 wt % yield of the protein extracted from the Linola seed meal. The dried Linola protein isolate had a protein content of 112 wt % (N×6.25) d.b.

The clarified supernatant was concentrated using 300 daltons molecular weight cut-off membranes to 1.25 L of concentrated supernatant containing 63.3 g/L of protein. The concentrated supernatant was dried and produced 77 g of a Linola protein isolate (20% yield) having a protein content of 106 wt % (N×6.25) d.b.

High pressure liquid chromatography (HPLC) analysis was performed as described in copending U.S. patent application Ser. No. 10/413,371 filed Apr. 15, 2003 (WO 03/088760), assigned to the assignee hereof and the disclosure of which is incorporated herein by reference, on the two Linola fractions.

Example 6

This Example illustrates the functional properties of the PMM-derived and supernatant-derived Linola protein isolates produced in Example 5.

The PMM-derived and supernatant-derived Linola protein isolates prepared according to the procedures of Example 5 were tested for functional properties of foaming and oil holding capacity, according to the procedures described in Example 4, in comparison to typical PMM-derived and supernatant-derived canola protein isolates (CPI) produced according to the process described in the aforementioned U.S. patent application Ser. No. 10/137,391 (W002/089597).

The results obtained are set forth in the following Tables V and VI:

TABLE V

Linola Protein Isolate vs. Canola PMM-derived CPI

| Batch | % Overrun (Foam Volume) | Foam Stability (Ml drainage at 15 minutes) | Oil Holding Capacity (Ml oil/100 mg protein) | Globular size (µM) |
|---|---|---|---|---|
| CPI-1 | 1471.8 | 17.5 | 147.7 | 18.9 |
| CPI-2 | 1030.4 | 32.7 | 190.5 | 29.1 |
| CPI-3 | 1216.5 | 24.0 | 119.8 | 24.3 |
| CPI-4 | 1051.2 | 45.3 | 115.4 | 21.6 |
| CPI-5 | 1091.6 | 35.3 | 124.5 | 28.0 |
| CPI-6 | 1196.1 | 34.0 | 166.9 | 24.6 |
| PMM-derived Linola | 1464.0 | 2.0 | 139.5 | 19.8 |
| Supernatant-derived Linola | 1470.0 | 0 | 81.4 | 11.8 |

TABLE VI

Linola Protein Isolate vs. Canola Supernatant-derived CPI

| Batch | % Overrun (Foam Volume) | Foam Stability (Ml drainage at 15 minutes) | Oil Holding Capacity (Ml oil/100 mg protein) | Globular size (µM) |
|---|---|---|---|---|
| CPI-7 | 2603.6 | 22.7 | 67.2 | 72.6 |
| CPI-8 | 1984.8 | 21.3 | 53.6 | 151.7 |
| CPI-9 | 1924.4 | 22.0 | 43.3 | 151.7 |
| CPI-10 | 1889.2 | 17.3 | 41.3 | 192.4 |
| CPI-11 | 2776.8 | 4.0 | 47.1 | 118.9 |
| PMM-derived Linola | 1464.0 | 2.0 | 139.5 | 19.8 |
| Supernatant-derived Linola | 1470.0 | 0 | 81.4 | 11.8 |

As may be seen from Tables V and VI, the functional properties of the PMM-derived and supernatant-derived Linola protein isolate were very similar, as might be expected from their similar HPLC properties, the main differences being in emulsion characteristics, differences lying between the two fractions in oil holding capacity and globular size.

In most categories, the functionality of the PMM-derived and supernatant-derived Linola protein isolates was as good or better than the PMM-derived and supernatant-derived canola protein isolates. The PMM-derived and supernatant-derived Linola protein isolate was weaker than the canola supernatant-derived isolate in foam volume, but the stability of the Linola foam was much better.

Example 7

This Example illustrates analysis of the PMM-derived and supernatant-derived Linola protein isolates produced in Example 5.

Figure 2:
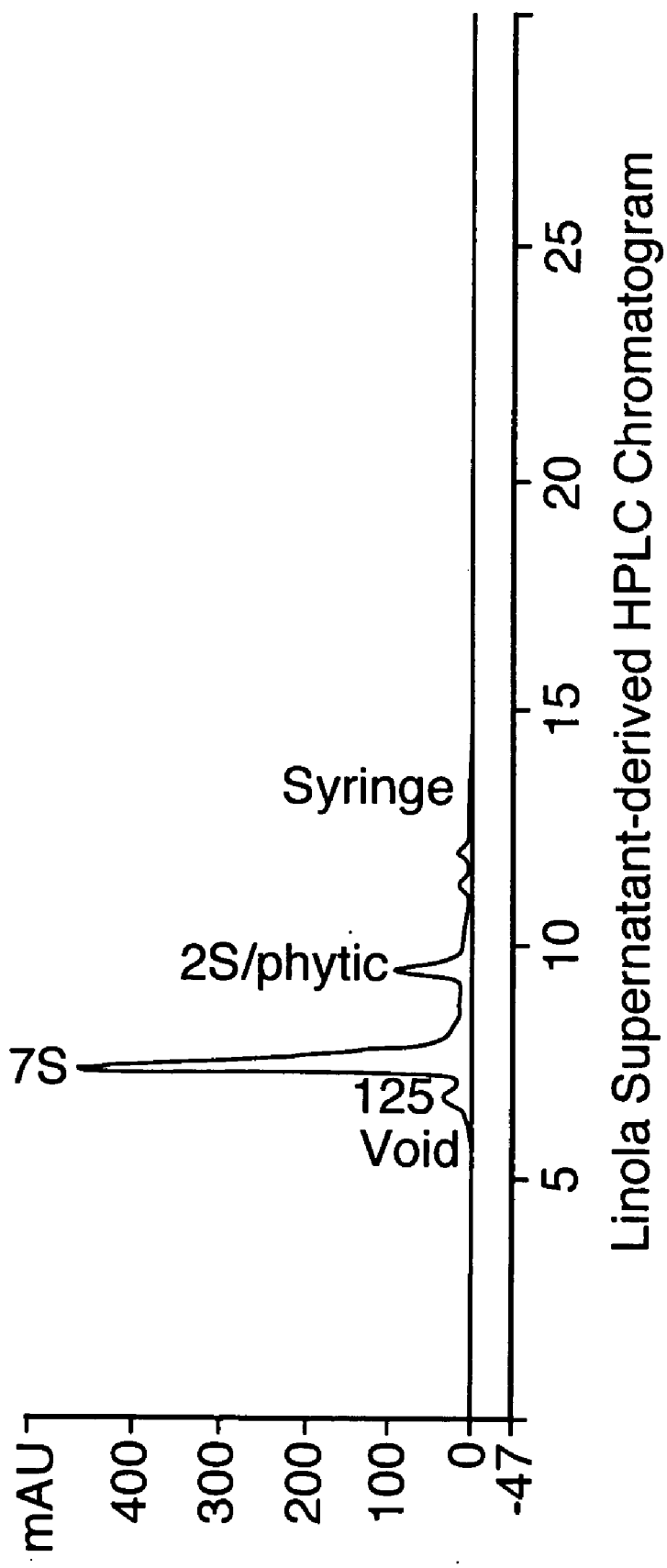

HPLC analysis, performed as described in co-pending U.S. patent application Ser. No. 10/413,371 filed Apr. 15, 2003 (WO 03/088760), assigned to the assignee hereof and the disclosure of which is incorporated herein by reference, of the two Linola isolates showed that each isolate is made up primarily of the same components, as may be seen in FIGS. 1 and 2. In both Linola protein isolates, the main protein component has a molecular weight of approximately 162,000 to 169,000 Da with lesser components, one having a molecular weight in the range of 16,000 to 17,000 Da and another having a molecular weight of 415,000 to 440,000 Da. These results are summarized in the following Tables VII and VIII:

TABLE VII

HPLC Profiles for PMM-Derived Linola Protein Isolate

| Protein Fractions | 12S - Linin | 7S - Half Linin | 2S - Colinin | Others |
|---|---|---|---|---|
| % of Protein Peaks | 11.9 | 78.0 | 9.2 | 0.9 |
| M.W. in kDa | 415-440 | 162-169 | 16-17 | |

TABLE VIII

HPLC Profiles for Supernatant-Derived Linola Protein Isolate

| Protein Fractions | 12S - Linin | 7S - Half Linin | 2S - Colinin | Others |
|---|---|---|---|---|
| % of Protein Peaks | 6.4 | 76.9 | 12.6 | 4.1 |
| M.W. in kDa | 415-440 | 162-169 | 16-17 | |

Example 8

This Example illustrates amino acid analysis.

Linola protein isolates prepared as described in Examples 3 and 5 were analyzed for amino-acid content.

The amino acid analysis is set forth in the following Table IX:

TABLE IX g/100 g dry matter

| Amino Acid MW(1) | Amino Acid | PMM-derived isolate | Supernatant-derived isolate | IEP-derived isolate |
|---|---|---|---|---|
| 133.1 | Aspartic | 11.50 | 11.40 | 11.90 |
| 119.1 | Threonine | 3.97 | 3.80 | 3.77 |
| 105.1 | Serine | 4.74 | 4.87 | 4.88 |
| 204.2 | Tryptophan | 1.84 | 1.81 | 1.75 |
| 146.1 | Glutamic | 21.10 | 21.00 | 19.10 |
| 75.1 | Glycine | 5.61 | 5.62 | 5.26 |
| 89.1 | Alanine | 4.67 | 4.78 | 4.90 |
| 121.1 | Cystine | 1.30 | 1.28 | 0.96 |
| 117.1 | Valine | 5.30 | 5.70 | 5.92 |
| 149.2 | Methionine | 1.47 | 1.42 | 1.48 |
| 131.2 | Isoleucine | 4.33 | 4.49 | 4.93 |
| 131.2 | Leucine | 5.33 | 5.36 | 5.76 |
| 181.2 | Tyrosine | 2.29 | 2.36 | 2.25 |
| 165.2 | Phenylalanine | 4.85 | 4.86 | 5.86 |
| 155.2 | Histidine | 2.03 | 2.02 | 2.09 |
| 146.2 | Lysine | 2.73 | 2.34 | 2.69 |

TABLE IX-continued g/100 g dry matter

| Amino Acid MW(1) | Amino Acid | PMM-derived isolate | Supernatant-derived isolate | IEP-derived isolate |
|---|---|---|---|---|
| 174.2 | Arginine | 11.80 | 12.10 | 12.20 |
| 115.1 | Proline | 3.71 | 3.87 | 4.05 |
| | Sum: | 98.57 | 99.08 | 99.75 |
| | Avg. aa MW(1) | 134.75 | 135.33 | 136.43 |
| | Anhydrous MW(2) | 116.74 | 117.32 | 118.41 |

Note:
(1)Molecular Weight of "free" amino acids.
(2)Weight Average Molecular Weight of polymeric amino acids.
Note:
No adjustment made for Glutamine or Asparagine, which are included in Glutamic and Aspartic respectively.

The values presented in Table IX represent amino acids on the basis of grams per 100 grams dry weight. The data was adjusted to the basis of 100 grams of amino acid and the revised data is shown in the following Table X:

TABLE X

Amino Acid Summary: g/100 g Amino Acids

| Amino Acid | PMM-derived isolate | Supernatant-derived isolate | IEP-derived isolate |
|---|---|---|---|
| Aspartic* | 11.7 | 11.5 | 11.9 |
| Threonine[e] | 4.0 | 3.8 | 3.8 |
| Serine | 4.8 | 4.9 | 4.9 |
| Tryptophan[e] | 1.9 | 1.8 | 1.8 |
| Glutamic* | 21.4 | 21.2 | 19.1 |
| Glycine | 5.7 | 5.7 | 5.3 |
| Alanine | 4.7 | 4.8 | 4.9 |
| Cystine[e] | 1.3 | 1.3 | 1.0 |
| Valine[e] | 5.4 | 5.8 | 5.9 |
| Methionine[e] | 1.5 | 1.4 | 1.5 |
| Isoleucine[e] | 4.4 | 4.5 | 4.9 |
| Leucine[e] | 5.4 | 5.4 | 5.8 |
| Tyrosine | 2.3 | 2.4 | 2.3 |
| Phenylalanine[e] | 4.9 | 4.9 | 5.9 |
| Histidine[e] | 2.1 | 2.0 | 2.1 |
| Lysine[e] | 2.8 | 2.4 | 2.7 |
| Arginine[e] | 12.0 | 12.2 | 12.2 |
| Proline | 3.8 | 3.9 | 4.1 |
| Sum: | 100.0 | 100.0 | 100.0 |
| Sum essential aa: | 45.6 | 45.6 | 47.5 |

[e] = 11 essential amino acids
aa = amino acids
*Glutamic acid and aspartic acid include glutamine and asparagine respectively As may be seen from Table 1× and Table IX, the amino acid profiles for PMM-derived, supernatant-derived and IEP-derived Linola protein isolates are very similar.

Table IX includes the molecular weights for the individual amino acids. Combined with the individual quantities, the average molecular weights for the "free" amino acids for the three protein isolates are shown, and are all about 135 Da. The anhydrous Weight Averaged Molecular Weights are also shown since the proteins are biopolymers of anhydrous amino acids, (each minus a water molecule, excluding one terminal amino acid per polypeptide). The average polymeric amino acid molecular weights are all about 117 to 118 Da. Table X also indicates the essential amino acids, which cannot be synthesized by humans. The overall content of the eleven essential amino acids is very similar for the three protein isolates.

Example 9

This Example illustrates Differential Scanning Calorimetry analysis of Linola protein isolates.

Linola protein isolates prepared as described in Examples 3 and 5 were subject to Differential Scanning Calorimetry. Differential Scanning Colorimetry is an instrumental method that measures the phase transition that arises for bio-molecules. The sample is placed into a sealed pan with some water or buffered solution and heat is applied at a constant rate, such as 10° C./minute, covering a specific temperature range, such as 20° C. to 150° C. A second pan, containing water or buffer solution, is simultaneously heated to act as a reference. A thermogram of the energy uptake, called endothermic heat flow, is recorded during the temperature rise. Complex biologicals, such as proteins, absorb energy and this energy changes the conformation of the molecule, denaturing or unfolding it. Denaturation behavior is specific for individual proteins, or other bio-molecules, and the analysis provides the Denaturing Temperature, $T_D$ and the enthalpy change ($\Delta H$) in Joules/gram of sample. The thermogram shows an energy "well" representing the phase transition from the native to denatured protein. The bottom of the "well" represents the $T_D$ value. The absence of any energy "well" indicates that complete denaturing has occurred.

Figure 3:
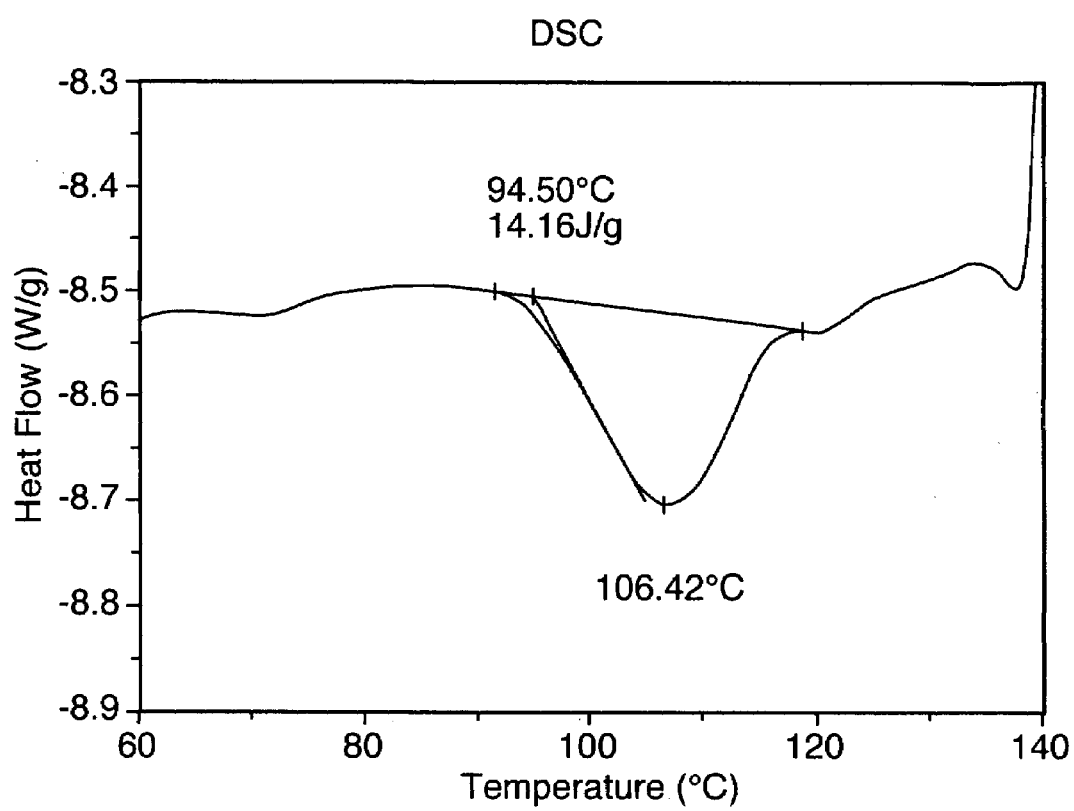
FIGS. 3, 4 and 5 are Differential Scanning Calorimetry thermograms for Linola isolates, with FIG. 3 being that for PMM-derived Linola protein isolate, FIG. 4 being that for a supernatant-derived Linola protein isolate and FIG. 5 being that for EP-derived Linola protein isolate.
Figure 4:
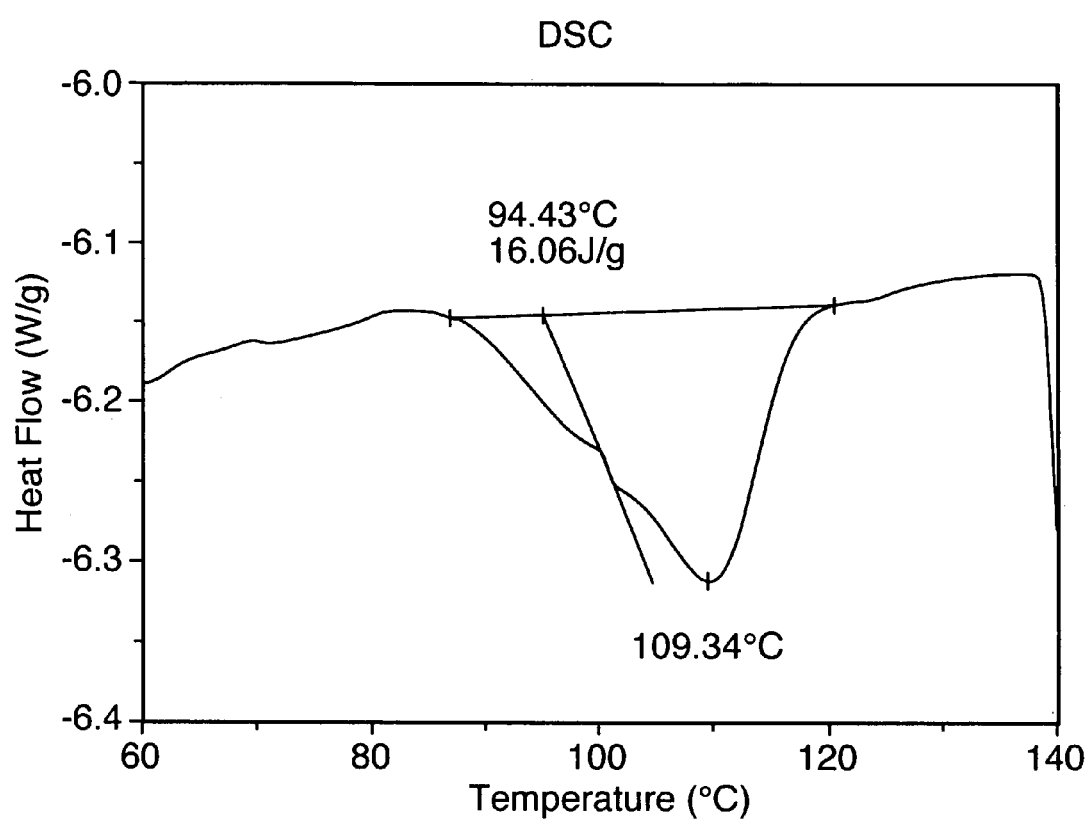
Figure 5:
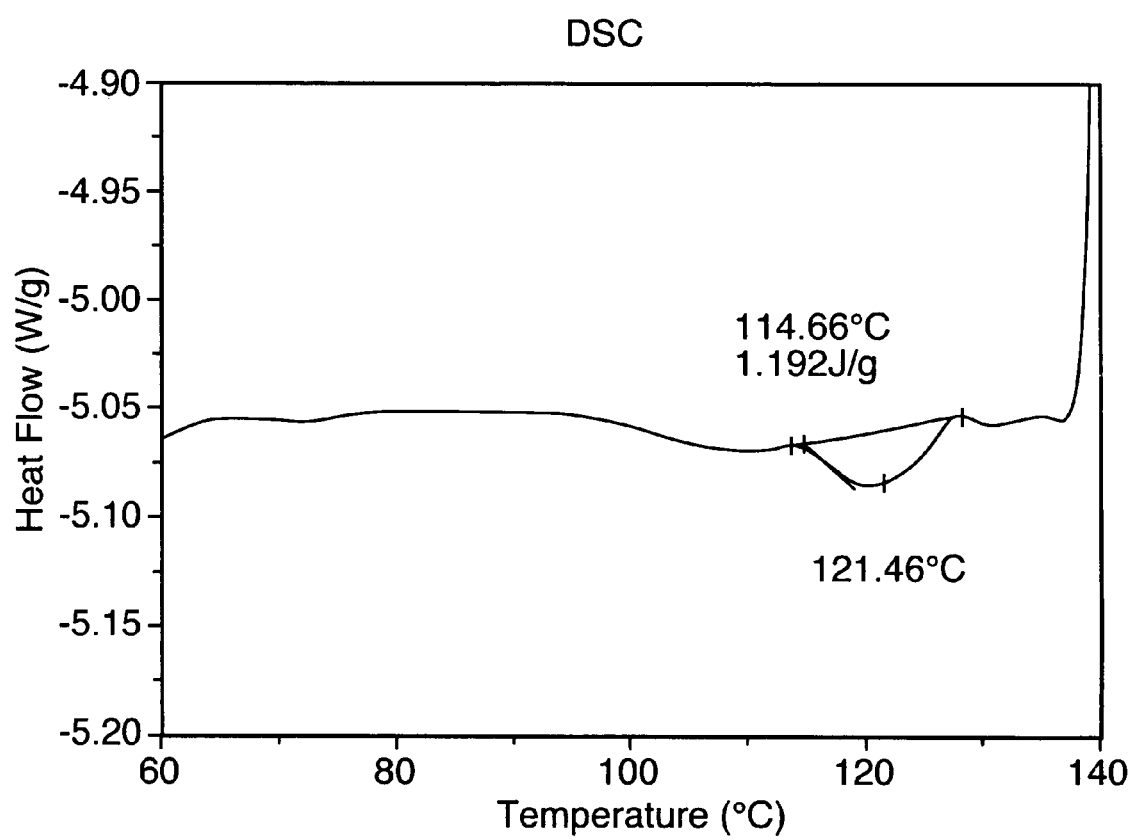

As may be seen from FIGS. 3, 4 and 5, PMM-derived and supernatant-derived Linola protein isolates are similar in terms of thermal stability, as might be expected from their similar HPLC properties, with supernatant-derived Linola protein isolate having a slightly higher stability. The Differential Scanning Calorimetry thermogram for IEP-derived Linola protein isolate indicates that this protein isolate is substantially denatured in contrast to the PMM-derived and supernatant-derived Linola protein isolates which are substantially undenatured.

SUMMARY OF DISCLOSURE

In summary of this disclosure, the present invention provides an improved method of producing flax protein isolates in which mucilage first is extracted from the flax oil seed prior to flax oil removal and flax oil seed meal preparation, enabling greater yields of protein isolates to be obtained and greater flexability in isolation procedure to be achieved. The present invention further provides novel flax protein isolates having a unique protein isolate. Modifications are possible within the scope of the invention.

We claim:

1. A process of preparig a flax protein isolate having a protein content of at least about 90 weight percent, as determined by Kjeldahl nitrogen times 6.25, which comprises:

initially extracting flax oil seeds to remove mucilage therefrom using a mildly-alkaline aqueous solution of an alkaline material, crushing the extracted oil seeds to recover oil and leave a meal, and processing the meal to recover a flax protein isolate therefrom by:

solubilizing protein in said flax oil seed meal by extracting using an aqueous sodium chloride solution having an ionic strength of at least about 0.10 M at a pH of about 5 to about 7 to provide an aqueous protein solution having a concentration of about 5 to about 40 g/L, concentrating the aqueous protein solution while maintaining the ionic strength substantially constant to a concentration of at least about 150 g/L by a selective membrane technique, diluting the concentrated protein solution with water having a temperature of less than about 15° C. to form protein micelles, and collecting and recovering said protein micelles as a protein micellar mass of flax protein isolate.

2. The process of claim 1 wherein said mildly-alkaline solution has a pH of about 7.5 to about 9.

3. The process of claim 2 wherein said initial extraction of oil seeds to remove mucilage therefrom is effected by an aqueous solution of sodium bicarbonate.

4. The process of claim 1 which is effected at a temperature of about 30° to about 70° C.

5. The process of claim 2 which is effected at a temperature of about 50° C.

6. The process of claim 1 which is effected at a seed to solution ratio of about 1:1 to about 1:20.

7. The process of claim 2 which is effected at a seed to solution ratio of about 1:5 to about 1:10.

8. The process of claim 1 wherein the aqueous solution has a concentration of about 0.2 to about 0.7 M of mildly-alkaline material.

9. The process of claim 1 which is effected by stirring the oil seed in the aqueous solution for about 15 to about 60 minutes.

10. The process of claim 2 which is effected by stirring the oil seed in the aqueous solution for about 30 to about 60 minutes.

11. The process of claim 1 wherein there are multiple extractions of the oil seed until no further mucilage is extracted from the oil seeds.

12. The process of claim 1 wherein said mildly-alkaline material is sodium bicarbonate.

13. The process of claim 1 wherein said initial extraction of oil seeds to remove mucilage therefrom is effected by stirring the oil seeds for about 15 to about 60 minutes in an aqueous solution of sodium bicarbonate having a pH of about 6.0 to about 7.5 at a temperature of about 30° to about 70° C. and at a seed to solution ratio of about 1:1 to about 1:20.

14. The process of claim 13 wherein said aqueous solution of sodium bicarbonate has a concentration of about 0.2 to about 0.7M said oil seeds to solution ratio is about 1:5 to about 1:10 and the stirring is effected from about 30 to about 60 minutes, and multiple extractions of the oil seed are effected until no further mucilage is extracted from the oil seeds.

15. The process of claim 13 which is carried out using an about 0.5 M aqueous solution of sodium bicarbonate having a concentration of about 0.5 M at about 50° C. and at a seed to solution ratio of about 1:10.

16. The process of claim 1 wherein the protein micellar mass is dried.

17. The process of claim 1 wherein residual liquid from the recovering of the protein micellar mass is processed to recover additional quantities of flax protein isolate.

* * * * *